United States Patent
Nilsson

(10) Patent No.: US 7,700,746 B2
(45) Date of Patent: *Apr. 20, 2010

(54) FILTRATION MATERIAL

(75) Inventor: Kurt Nilsson, Lund (SE)

(73) Assignee: Glycorex Transplantation AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/743,269

(22) Filed: Dec. 23, 2003

(65) Prior Publication Data

US 2004/0242857 A1 Dec. 2, 2004

Related U.S. Application Data

(63) Continuation-in-part of application No. 09/722,241, filed on Nov. 27, 2000, now Pat. No. 6,686,457, which is a continuation-in-part of application No. 09/091,486, filed on Jun. 19, 1998, now Pat. No. 6,444,655.

(30) Foreign Application Priority Data

| Feb. 8, 2000 | (SE) | ..................................... 0000430 |
| Jun. 28, 2000 | (SE) | ..................................... 0002462 |
| Nov. 24, 2000 | (SE) | ..................................... 0004343 |

(51) Int. Cl.
*C07H 15/00* (2006.01)
*A61K 31/70* (2006.01)

(52) U.S. Cl. ................ 536/4.1; 536/123.1; 536/123.13; 536/120; 536/53; 514/25

(58) Field of Classification Search .................. 536/4.1, 536/123.1, 123.13, 120, 53; 514/25
See application file for complete search history.

(56) References Cited

U.S. PATENT DOCUMENTS

| 4,839,290 | A | * | 6/1989 | Kaieda et al. | ................ 435/377 |
| 5,935,940 | A | * | 8/1999 | Weisz | ........................... 514/58 |
| 5,962,422 | A | * | 10/1999 | Nagy et al. | ................... 514/25 |
| 6,444,655 | B1 | * | 9/2002 | Nilsson | ...................... 514/61 |
| 6,686,457 | B1 | * | 2/2004 | Nilsson | ...................... 536/4.1 |

OTHER PUBLICATIONS

Callahan et al., Immunological Communications, (1975) 4(6), pp. 537-552 (Abstract Sent).*
Bergami et al. (European Journal of Applied Microbiology and Biotechnology, (1979), 7(1), 53-57) (Abstract Sent).*
Lisman et al. (Hoppe-Seyler's Zeitschrift fuer Physiologische Chemie (1978), 359 (8), 1019-22, Abstract Sent).*
Lisman et al. (Hoppe-Seyler's Zeitschrift fuer Physiologische Chemie (1978), 359 (8), 1019-22).*

* cited by examiner

*Primary Examiner*—Shaojia Anna Jiang
*Assistant Examiner*—Michael C Henry
(74) *Attorney, Agent, or Firm*—Smith Gambrell & Russell LLP

(57) ABSTRACT

Material characterized by that the material contains at least one biologically active di- or trisaccharide or higher oligosaccharide which is covalently bound via a spacer to cross-linked agarose.

9 Claims, No Drawings

FILTRATION MATERIAL

The present application is a continuation-in-part of U.S. application Ser. No. 09/722,241, filed Nov. 27, 2000, now U.S. Pat. No. 6,686,457, which is a continuation-in-part of U.S. application Ser. No. 09/091,486, filed Jun. 19, 1998 (U.S. Pat. No. 6,444,655, issued Sep. 23, 2002) and which is incorporated herein by reference in their entirety. This application claims priority from Swedish Application No. 0002462.0, filed Jun. 28, 2000, Swedish Application No. 0000430.9, filed Feb. 8, 2000 and Swedish Application No. 0004343.0, filed Nov. 24, 2000.

SUMMARY OF THE INVENTION

The present invention relates to a filtration material comprising a matrix that is bound via a spacer to a saccharide. The filtration material filters e.g. blood group A-antibodies, blood group B-antibodies, or other targeted substances that are to be filtered from for example blood e.g. before and/or during and/or after transplantation to prevent blood group incompatibility problems between a donor and a recipient. The inventive material, however, is not restricted to blood group incompatibility transplantation. The inventive material can be used in a variety of blood filtering applications, such as production of blood plasma with reduced content of anti-A and/or anti-B antibodies, thus enabling the production of a plasma which can be given irrespective of the blood group of the recipient, and can even be used to reduce problems of tissue type mismatch or mismatch of the HLA system between donor and recipient. In addition to blood filtering, the filtration material could also be used in a variety of filtering application relating to food, water, viruses, and protein separation. The filtering of blood or blood plasma occurs by passage of blood or plasma through at least one column or filter or other filtration device that contains the inventive material. The inventive filtration material allows the combination of high flow rate, minimal drop in pressure over the column, and a good binding capacity.

DETAILED DESCRIPTION OF THE PREFERRED EMBODIMENTS

The active part of the filtration material according to the invention, contains one saccharide part which has been bound via a spacer to a matrix according to the following formula:

saccharide-spacer-matrix.

The saccharide-spacer portion of the material is referred to as a ligand. In the description below, saccharide-spacer and ligand is also used for situations where the saccharide is linked to a spacer molecule which constitutes one part of the final spacer between saccharide and matrix, and the saccharide-spacer or ligand is used for coupling to the activated matrix or to activated matrix or to activated spacer-matrix (where spacer constitutes another part of the final spacer between saccharide and matrix, spacer-matrix may be for example aliphatic/aromatic compound-matrix, protein-matrix, peptide-matrix or other type of compound linked to matrix) to form the final saccharide-spacer matrix. Thus, the saccharide-spacer in these situations contain for example an amino (NH2-) group, a carboxyl group or another reactive group, which is reacted with the matrix or the spacer-matrix containing reactive groups.

The matrix can have a wide range of bound molecules of ligand. It is possible to have two or more molecules of bound saccharide attached to the matrix. The amount of bound saccharide can also be 0.01, 0.1, 1, 2, 3, 4, 5, 6, 7, 8, 9, 10, 11, 12, 13, 14, 15, 16, 17, 18, 19 or 20 mmole per liter of matrix or an amount of mmole which is between two of the above given values per liter of matrix.

The ligand can also contain a protein or a polysaccharide as the spacer, or as a part of the spacer, between the saccharide and matrix. For example, a protein such as serum albumin, or a polysaccharide, such as dextran could be used. The saccharide could be coupled first to the protein or the polysaccharide that is selected and then the resulting ligand is coupled to the matrix. The same type of chemistry can be used to achieve linkages between saccharide, protein, or polysaccharide, and the matrix. Using a peptide, protein, or polysaccharide can have the benefit of increasing the protein binding ability of the filtration material, which results in increased efficiency.

In a variant of the invention, hydroxyethylamino-groups or Tris-groups (tris(hydroxymethyl)aminomethane-group) is included in the material. The hydroxyethylamine group and/or the Tris group may be included by for example reacting the saccharide-spacer-matrix with a solution containing hydroxylethylamine and/or Tris (tris(hydroxymethyl)aminomethane) at suitable conditions of temperature, pH and reaction time. Thus, for example after reaction of ligand and activated matrix to obtain saccharide-spacer-matrix a Tris-solution is reacted with remaining reactive groups on the matrix, such as NHS-activated carboxyl groups, by e.g. washing the saccharide-spacer-matrix on e.g. a glass filter, with a Tris-HCl buffer and allowing coupling to proceed at suitable pH and temperature and time, under e.g. sterile or semi-sterile conditions or other conditions. This treatment also leads to a reduction of any remaining reactive groups on the material. The Tris-HCl buffer can optionally first have been filtered through a filter having a suitable molecular cut-off (e.g, a cut off of molecular weights of ca. 3000, 5000, 10000, 30000 or 0.5 mikrometer, thus allowing penetration of smaller molecules than the cut off value, or any value between these values) to reduce contaminants, endotoxins and/or pathogens. Alternatively, or as a complement to the filtration, the Tris-HCl buffer can first have been autoclaved. As a result, the filtration material contains hydroxyethylamino groups or $(HOCH_2)_3C$—NH-groups (Tris-groups) bound covalently to e.g. a carbonyl group (—CO—) linked directly to the matrix or via a suitable spacer to the matrix such as —$CO(CH_2)_m$—NH—$CH_2$—CH(OH)—$CH_2$—O—, where m is for example 1, 2, 3, 4, 5, 6, 7 or 8, leading to formation of $(HOCH_2)_3C$—NH—$CO(CH_2)_m$NH—$CH_2$—CH(OH)—$CH_2$—O-matrix.

The term, saccharide, as used in accordance with this invention is defined as a carbohydrate containing molecule or derivative thereof as exemplified below that has biological or some other sort of affinity to another molecule, protein, or cell. The saccharide could thus be a biologically active disaccharide, trisaccharide, tetrasaccharide or pentasaccharide, or higher oligosaccharide substances. Examples of saccharide according to the invention include for example the types of saccharides and fragments thereof which are linked to lipids as in glycolipids, to proteins as in glycoproteins, saccharides produced by enzymatic synthesis, recombinant techniques, by chemical synthesis, isolation from natural sources or by a combination of these methods, glycoprotein, neoglycoprotein, glycopeptide, glycosylated amino acid, or any of these which contains a part, fragment, or a modified variant thereof The saccharide, can for example be selected from monosaccharides such as Gal, Man, Glc, 5-NeuAc, GlcU, GalU, GlcNAc, GalNAc, any of these modified in one or more of its hydroxyl groups or N-Acetyl group with an aromatic and/or an aliphatic group, and which are linked O-, N-, S- or C-glycosidically or α- or β-configuration to the spacer, from di-, tri-, tetra-, penta- or higher oligosaccharide comprising one or more of Gal, Man, Glc, 5-NeuAc, GlcU, GalU, GlcNAc, GalNAc monosaccharide units, and/or one or more of these modified in one or more of its hydroxyl group(s) or N-Acetyl group(s) with an aromatic and/or an aliphatic group, and where the monosaccharide units are α- and/or β-glycosidically linked to each other in the di-, tri-, tetra-, penta- or higher oligosaccharide and where the terminal monosaccharide unit in the saccharide is O-, N-, S-, or C-glycosidically in α- or β-configuration to the spacer. As a few non-limiting examples may be mentioned blood group determinants A and B, Galα1-3Galα-, Galα1-3Galβ-, Galα1-3Galβ1-4Glcβ-, Galα1-3Galβ1-4GlcNAcβ-, Galα1-3Galβ1-4GlcNAcβ1-3Galβ1-4Glcβ-, or of oligomeric ligands, such as for example (Galα1-3Galα-)n-, (Galα1-3Galβ-)n-, (Galα1-3Galβ1-4Glcβ-)n-, (Galα1-3Galβ1-4GlcNAcβ-)n-, (Galα1-3Galβ1-4GlcNAcβ1-3Galβ1-4Glcβ-)n-, or (Galα1-3Galα1-spacer)n-, (Galα1-3Galβ-spacer)n-, (Galα1-3Galβ1-4Glcβ-spacer)n-, (Galα1-3Galβ1-4GlcNAcβ-spacer)n-, (Galα1-3Galβ1-4GlcNAcβ1-3Galβ1-4Glcβ-spacer)n-, n is an integer larger than 1. Other non-limiting examples of saccharides include antigens of type Lewis-a, Lewis-b, Lewis-x, or Lewis-y, sialylated Lewis antigen, fragments of the repeating structure of heparin, Galα1-4Gal, GalNAcα-.

The Galα1-3Gal types of saccharide can be of interest for example in a column, for example, before or after xenotransplantation to reduce antibodies reactive towards these antigens from the patient's blood (whole blood column) or plasma, or for isolation of said type of antibodies. This type of product can also be of interest to use in combination with other products mentioned in this application, e.g., for removal of anti-B and anti-A antibodies together with blood group A and/or blood group B containing material.

Material containing the blood group A and blood group B determinants can for example also be of interest for production of immunoglobulins with reduced content of antibodies specific towards the blood group A and B determinants (anti A and anti B antibodies by treatment of crude or purified immunoglobulin fractions obtained from human blood, for reducing the content of anti-A and anti-B antibodies in human blood plasma, for reduction of said antibodies before and/or after transplantation of a blood group incompatible organ to a recipient of another blood group.

Other carbohydrate structures specific for toxins, viruses, bacteria and or cells could also be used in the formation of the filtration material. Such saccharides specific for pathogens, toxins, viruses, bacteria and cells are defined in the literature and can be used to obtain saccharide-spacer-matrix according to what is described in this description. The filtration material could then be used to purify, isolate or eliminate virus and/or bacteria from whole blood, plasma, food products, water, or from other materials.

Other carbohydrate structures (of which several such structures are known from the literature, see for example Taylor and Drickamer, Introduction to Glycobiology, Oxford, 2003 and referenced cited therein) active towards antibodies, for example, antibodies against cancer antigens such as prostrate, breast, intestine, or skin cancer, saccharides known to bind to other proteins than antibodies or to toxin, virus or bacteria could be used when bound glycosidically to a spacer. The saccharide-spacer is coupled to matrix according to the invention to form the material according to the invention. The resulting material could be used as a filter or a device containing the material to bind the mentioned type of antibody, protein, toxin, virus, bacteria or cell from a liquid such as blood or blood plasma or from another type of liquid, or reaction mixture, obtained for example in connection with cell mediated production including or not including recombinant techniques, containing the mentioned type of antibody, protein, toxin, virus, bacteria or cell.

After contacting the material according to the invention with the liquid containing the protein, antibody, toxin, virus, bacteria or cell, or blood or blood plasma, the bound antibody, protein, toxin, virus, or bacteria could optionally be eluted from the material according to the invention. The material according to the invention may after equilibration with a buffer or liquid of a suitable pH for binding be used again. Thus, the material can be used more than one time and repeatedly several times. Optionally the material can be sterilized between uses by using heat treatment such as autoclaving, steam sterilization and/or treatment at high pH for example of pH 12 or higher with e.g. a sodium hydroxide solution.

The bound protein, antibody, toxin, virus or cell can be isolated after elution from the filtration material. The elution buffer may be of lower pH such as for example glycine buffer of pH 2.2 or similar pH suitable for the elution. The eluted antibodies or proteins could be used in different type of applications such as research, the treatment of disease, for immunization, to produce vaccines or in reagents. The filtration material could also be used to remove undesired protein or antibody from solutions, blood or human plasma, for example for removal of antibody derivatives from blood or plasma in connection with for example immunotherapy of cancer patients.

The spacer can be varied and is chosen by the expert. A non-limiting example of the spacer is —O(CH$_2$)$_n$PhNH—CO—(CH$_2$)$_m$NH—CH(OH)—CH$_2$—, wherein n is 0, 1, 2, 3, or 4 and m is 1, 2, 3, 4, 5, 6, 7 or 8 and the reducing end of the saccharide is bound α or β-glycosidically to the spacer, i.e. the product contains Saccharidea-O(CH$_2$)$_n$PhNH—CO—(CH$_2$)$_m$NH—CH(OH)—CH$_2$-Matrix or Saccharideβ-O(CH$_2$)$_n$PhNH—CO)CH$_2$)$_m$NH—CH(OH)—CH$_2$-Matrix.

Instead of the —O(CH$_2$)$_n$PhNH— group, the spacer or part of the spacer could also include —O(CH$_2$)$_n$NH (n is an integer, for example 1, 2, 3, 4, 5, 6, or 7). It is also possible to use other aliphatic compounds or aromatic compounds as a part of the spacer or as the spacer. A saccharide such as the blood group A- or B-determinant could be optionally bound to an oligomeric substance acting as a spacer, such as a peptide, oligo- or polysaccharide, protein, an oligo- or multifunctional compound. The peptide, for example, can for example consist of amide-bound glycine and glutamic acid residues, such as Gly-(Glu-Gly)$_n$-Glu, where n is an integer from 1 to 20. The linkage between the succharide and peptide can then, for example, be via a —O(CH$_2$)$_n$PhNH— group (i.e. saccharide-O(CH$_2$)$_n$PhNH-peptide) or a —O(CH$_2$)$_m$NH group. If bound to the —O(CH$_2$)$_m$NH group, the NH-part would then be bound to the carboxyl group on the side chain of the Glu-residues in the peptide via a NH—CO— (amide) linkage. The —O part of the —O(CH$_2$)$_n$PhNH— group or the —O(CH$_2$)$_m$NH group would be bound glycosidically to the saccharide.

The peptide can optionally be coupled to activated matrix, such as for example agarose or activated cross-linked agarose, for example NHS-activated agarose, for example NHS activated Sepharose® 4FF (where NHS is a N-hydroxysuccinimide which is activating the COOH group) via the α-amino group on the peptide so that an amide linkage is formed between the amino group of the peptide and a carboxyl group linked directly or via a spacer to the matrix, and thereafter can the saccharide be bound via Saccharide-O(CH$_2$)$_n$PhNH—, or Saccharide-O(CH$_2$)$_m$NH— to the carboxyl group on the Glu-residues in the peptide. This linkage between saccharide and Glu-residues can be achieved by, for example, carbodiimide-mediated coupling or by, for example, succinimide-mediated coupling. Another example of peptide is as above, but containing at least one Lysine residue, where the α-amino group in the peptide is used for covalent coupling to, for example, NHS-activated cross-linked agarose such as commercially available cross-linked Sepharose or Sepharose® 4FF (FF is for Fast Flow), with subsequent coupling of, for example, Saccharide-O(CH$_2$)$_n$PhNH— or Saccharide-O(CH$_2$)$_m$NH, to the peptide according to above. Other linkages could also be used according to the invention.

As another non-limiting example, a peptide consisting of amide bound Gly and Lys units, for example Gly-(Lys-Gly)$_n$-Gly, where n is an integer between 1 and 20 could be used. In this case, the peptide can be bound to the saccharide via amino groups on the peptide, a N-glycosidic linkage is formed between the reducing end on the saccharide and the α-amino group on the Lysine residue(s), and the saccharide-peptide can be coupled to the matrix by the terminal COO— group on the peptide and amino groups linked directly or via a spacer to the matrix (via for example carbodiimide, or succinimide coupling). In the same manner as the Gly-Glu-peptide, aliphatic or aromatic spacer can also be used to bind the saccharide to the Lysine residues of the peptide, but in this case glycosidically bound groups of the type —O(CH$_2$)$_2$Ph-COO— or —O(CH$_2$)$_n$COO— could be used for carbodiimide- or succinimide-mediated coupling to obtain CO—NH— (amide) linkage between Saccharide-O(CH$_2$)$_2$PhCOO— or Saccharide-O(CH$_2$)COO—, where n is as mentioned above, and Lysine amino group residues in the peptide.

The coupling to the peptide can also be carried out by first coupling the saccharide part to one or more of the amino acids of the peptide and thereafter forming the peptide linkages.

The matrix can be a polymer, plastic, or a polysaccharide, and can bind a large number of saccharide-spacer units. The matrix, can for example, be a plastic filter, a plastic bag covered with the saccharide spacer, polymeric beads such as Dynabeads containing e.g. tosyl groups or COOH groups for binding, agarose, a cross-linked agarose, such as cross-linked agarose such as cross-linked Sepharose® or other commercially available agarose such as Sepharose® Fast flow. NHS-activated cross-linked agarose, such as NHS-activated Sepharose® Fast Flow can also be used (NHS- is an abbreviation of N-hydroxysuccinimide; this variant of agarose is relatively strongly crossed-linked, this and other types of cross-linked agarose and other matrixes are commercially available).

The NHS-activated matrix can be obtained commercially or can be prepared by for example reacting a carboxyl group containing matrix with for example a carbodiimide such as EDC and then reacting with N-hydroxysuccinimide followed by coupling of the saccharide-spacer containing an amino group thus forming a amide linkage. Alternative, the Saccharide-spacer can be coupled to the carboxyl groups of the spacer using carbodiimide, for example reaction of EDC with carboxyl groups and reacting with the Saccharide-spacer containing at least amino group. The reversed situation may also be used, i.e. carboxyl group containing saccharide-spacer and amino-group containing matrix. This represents standard chemical operations and the conditions are chosen by the expert. Epoxy- or tosyl-activated matrix such as epoxy-activated Sepharose® or tosyl-activated agarose or Sepharose can also be used.

For example, the NHS-activated matrix could be used for covalent binding of saccharide containing the spacer or part of the spacer, such as Blood group A-O(CH$_2$)$_n$PhNH$_2$—, Blood group B-O(CH$_2$)$_n$PhNH$_2$, Blood group A-O(CH$_2$)$_n$PhNH—CO—(CH$_2$)$_m$NH— or Blood group B-O(CH$_2$)$_n$PhNH—CO—(CH$_2$)$_m$NH$_2$ or other Saccharide-spacer, at e.g. a pH within the range of pH 4 to 10, for example at pH4, pH 7.0, pH 7.5 or pH 8.0, in for example 0.1M sodium acetate buffer, MES buffer, phosphate buffer, or in a buffer containing sodium phosphate or other suitable buffer salt in a concentration in for example the range of 0.001M to 1M or with a concentration within this range, for a reaction time of for example 20 minutes, or 1 hour, 2, 3, 4, 5, 6, 7 or for more hours, or for any reaction time between 1 minutes and one week, at 2-8 degrees C., at room temperature or at any temperature between zero and 99 degrees Celsius. In the formulas n is 0, 1, 2, 3, or 4 and m is 1, 2, 3, 4, 5, 6 or 7. The filtration material could thereafter be treated with e.g. a 0.05M, 0.1M, 0.15M, 02M, 0.25M, 0.5, 1M (or of a concentration within between any of these values) Tris-HCl buffer at e.g. pH 4, 6.0, pH 8.0 or pH 10.0 or any pH between any of these values as mentioned above to react with remaining reactive groups. The coupling procedure can optionally be performed in a clean room of the required clean room class according to the required GMP (Good Manufacturing Practice) standard, and all solutions used in the coupling procedure may be filtered (see above filtration of Tris-HCl solution) and/or autoclaved before their use in the coupling procedure if sterile conditions and sterile product material according to the invention are desired. The product may then be optionally autoclaved before its use. The exact conditions for coupling reactions and autoclaving and other sterilization are chosen by the expert and do not limit the scope of the invention.

The matrix particles can be chosen to be practically spherical. The particle size is chosen, for example, from a particle size range in the interval of 1-165 μm.

Non-limiting examples of the filtration material include for example Blood group A-O(CH$_2$)$_n$PhNH—CO—(CH$_2$)$_m$—O-matrix and Blood group B-O(CH$_2$)$_n$PhNH—CO—(CH$_2$)$_m$—O-matrix, Blood group A-O(CH$_2$)$_n$PhNH—CO—(CH$_2$)$_m$NH—CH$_2$—CH(OH)—CH$_2$—O-matrix and Blood group B-O(CH$_2$)$_n$PhNH—CO—(CH$_2$)$_m$NH—CH$_2$—CH(OH)—CH$_2$—O-matrix, where n and m are defined as above. Matrix denotes any type of matrix, such as those exemplified above and e.g. specifically, cross-linked agarose, for example of the type cross-linked Sepharose® or Sepharose® Fast Flow, where —O—(CH$_2$)$_n$PhNH—CO—(CH$_2$)$_m$—O— and —O(CH$_2$)$_n$PhNH—CO—(CH$_2$)$_m$NH—CH$_2$—CH(OH)—CH$_2$— is the spacer separating the matrix from the saccharide, such as the Blood group A- or the Blood group B-saccharide. Blood group A-O(CH$_2$)$_n$PhNH—CO—(CH$_2$)$_m$—O—, Blood group B-O(CH$_2$)$_n$PhNH—CO—(CH$_2$)$_m$—O—, or Blood group A-O (CH$_2$)$_n$PhNH—CO—(CH$_2$)$_m$NH—CH$_2$—CH(OH)—CH$_2$— and Blood group B-O (CH$_2$)$_n$PhNH—CO—(CH$_2$)$_m$NH—CH$_2$—CH(OH)—CH$_2$— are non-limiting examples of ligands according to the invention.

Additional examples of the filtration material include: wherein the matrix is cross-linked agarose, n is selected from 1, 2, 3, or 4, m is selected from 1, 2, 3, 4, 5, 6, 7, or 8 and where the linkage between —O— and matrix is to a carbon atom in the matrix. Blood group A comprises GalNAcα1-3 (Fucα1-2)Galβ- and Blood Group B comprises GalNAcα1-3 (Fucα1-2)Galβ-. Specific examples include GalNAcα1-3 (FucαJ-2) Galβ-O(CH$_2$)$_2$Ph-NH—CO—(CH$_2$)$_5$NH—CH$_2$—CH (OH)—CH$_2$—O-matrix. Another example is GalNAcα1-3 (Fucα1-2)Galβ-O(CH$_2$)$_2$Ph-NH—CO—(CH$_2$)$_5$NH—CH$_2$—CH(OH)—CH$_2$—O-matrix.

Other examples containing a in the same manner bound, higher oligosaccharides, which contain the A- or B-determinant terminally, such as the blood group A- and B determinants of types 1, 2, 3, or 4, respectively. Further examples of the products are a combination of one or more blood group variants each bond via spacer to the matrix, i.e., the matrix contains both of e.g. the GalNAcα1-3 (Fucα1-2)Galβ-O—(CH$_2$)$_2$Ph-NH—CO—(CH$_2$)$_5$NH—CH$_2$—CH(OH)—CH$_2$—O— and (CH$_2$)$_5$NH—CH$_2$—CH(OH)—CH$_2$—O—matrix, or contains a combination of two or more different Saccharide spacer type of molecules e.g. saccharide and spacer of the types specified in this application.

Thus, a combination of ligands could be covalently bound to the matrix. For example, a combination of two or more different saccharides can be used to form ligands for attachment to the same matrix. For example, as a non-limiting example, a combination of Blood group A-O(CH$_2$)$_n$PhNH—CO—(CH$_2$)$_m$NH— and Blood group B-O(CH$_2$)$_n$PhNH—CO—(CH$_2$)$_m$NH— or of Blood group A-O(CH$_2$)$_n$PhNH—CO—(CH$_2$)$_m$NH—CH(OH)—CH$_2$—O— and Blood group B-O(CH$_2$)$_n$PhNH—CO—(CH$_2$)$_m$NH—CH(OH)—CH$_2$—O— could be attached to the same matrix. The saccharides can be different and the spacers can be different.

In the production of the filtration material, a commercially available matrix such as for example NHS-activated Sepharose® Fast Flow (NHS- is an abbreviation of N-hydroxysuccinimide; this variant of agarose is relatively strongly cross-linked), for example as is available in the form of practically spherical particles. The matrix is used for covalent binding of a Saccharide linked to a spacer at for example a pH of 6.0, 6.5, 7.0, 7.5, 8 in a buffer, such as for example 0.1 sodium phosphate, for 1 or 2 hours or up to for example 20 hours at room temperature or under other conditions exemplified above. The material is then washed on a glass filter or under other sterile conditions with buffer and treated with Tris-HCL buffer to react with remaining reactive groups. See also coupling conditions above for other optional conditions.

The inventive material can allow for a combination of high flow rate (for example in the interval 0.20 up to for example 1 ml/min and per ml of matrix), minimal drop in pressure over the column, and a good binding capacity not only of IgG antibodies but also of molecularly larger antibody or protein molecules such as 1 gM. As a non-limiting example can be mentioned single passage of more than one liter human blood group A plasma with a flow rate of about 40 ml per minute through 60 ml of filtering material, with an average particle size of 90 mikrometer, repeatedly, eliminated the majority of antibodies reactive against blood group B. Similar result was repeatedly obtained with blood group B plasma concerning antibodies toward blood group A. The products were built from cross-linked agarose such as Sepharose® 4Fast Flow.

One or more material according to the invention such as one or more filters, one or more columns can be used containing one or more of the materials according to the invention. The column volume is chosen for the purpose by the expert and can be for example of a size of for example in the range of 0.1 ml, 1 ml or higher or up to for example 100 liter volume of the inventive material, or any value between these values for example, 1, 10, 50, 60 ml, 120, one liter, 5 liter or 100 liter. The average particle size of the matrix can be for example be in the range of 1 to 250 mikrometer, or any value between these two values, for example 1, 5, 10, 30, 60, 90 or 250 mikrometer. As an example such a column with the material according to the invention, which optionally had been autoclaved, repeatedly, practically eliminated all antibodies against blood group B. In each cycle antibody was bound to the column and eluted with for example glycine buffer and/or alkaline solution such as sodium hydroxide buffer of for example pH 12 or higher. This allows preparation of columns for repeated use in the production of blood or plasma containing reduced amount of anti-A or anti-B antibodies, or for production of immunoglobulin with reduced content of anti-A or anti-B antibodies or both. Similar result was repeatedly obtained with blood group B plasma concerning antibodies towards blood group A. For example, passage of plasma with a flow rate of ca 40 ml/minute through a column with a production volume of 62 ml, and an average particle size of 90 mikrometer, practically eliminated all antibodies reactive against blood group A. Smaller or larger columns with the material according to the invention can be used depending on the quantity of liquid or blood or blood plasma desired to be processed.

Different types of column houses of different dimensions can be used for the product, and as an example may be mentioned a column house which has an inner volume between the porous membranes of about 62 ml (that is allows filling of 62 ml filtration material according to the invention).

When using filtration material according to the invention for treatment of liquid or plasma, membranes in the column which are used to prevent leakage of material from the column have a lower porosity than the size of the matrix particles. When using the filtration material according to the invention for treatment of whole blood, a membrane with porosity of 30 micrometer or 70 micrometer, or membrane with a porosity in the interval 20 to 100 micrometer can be used and the average particle size of the matrix can for example be 150 micrometer or the average matrix particle size can be for example in the interval 100-250 micrometer.

The column, completely or partially filled with filtration material according to the invention, can for example be constructed to allow autoclaving, steam sterilization, sodium hydroxide sterilization and/or for example to allow aseptic packing of filtration material according to the invention. Non-limiting example of autoclavable column is a column with two locks, both equipped with for example identical threads which are screwed, with help of the threads, outside and at both endings of a cylinder (house), which is equipped with matching threads at the two endings of the cylinder (house). Between each lock and cylinder is before screwing together locks and cylinder, placed a porous membrane (that is two membranes and rings for each column), which allows for passage for plasma or whole blood but not for passage of the filtration material according to invention. Each membrane is mounted between the lock and the cylinder with for example a silicon ring with a fitting grove of about the same or the same diameter as the cylinder. Every silicon ring has for example a grove which allows for fitting the circular membrane in the grove in the silicone ring. The membrane is therewith enclosed between the lock and the cylinder ending. The same procedure is carried out for the other ending of the cylinder. Each lock has a centrally placed hole with an elevation which allows for connecting a bio-compatible and autoclavable set of tubings equipped with connections of e.g. the Iner type.

Instead of connecting the locks and the cylinder with threads, can be used for example a clip mechanism, where the locks are equipped with one or more clips and the cylinder has on its outer side protruding edges placed below the upper part and above the lower end of the cylinder. In this manner the silicon ring and membrane according to the above can be placed between the lock and respective cylinder ending, and the locks are thereafter pressed on the cylinder, whereupon the clips are pressed under the protruding edges on the cylinder and stays there, and the silicon ring with the porous membrane is consequently sealed tightly between the lock and the cylinder.

In order to fill the so mounted column houses with filtration material according to the invention, the cylinder part is equipped with a circular opening with a protruding part, which has threads, on the outer side of the cylinder to allow connection of a tubing used for filling of the filtration material into the cylinder. The filling procedure is normally performed in a clean room of the required clean room class and under GMP, if a product is desired which is to be used in a clinical application. After filling of the filtration material in the column housing, a bio-compatible plug with threads which matches the threads of the protruding part of the cylinder. In the center of the plug is a protruding tap which its into the hold of the cylinder and which has a length which corresponds to the height of the protruding part. In this manner and (almost) flat surface is achieved inside the cylinder at the circular opening.

All mentioned components of the column house in the example with autoclavable column house, are autoclavable and/or can be sterilized with steam and/or can be sterilized with alkaline solution, and are bio-compatible. The method of for example autoclaving is normally chosen so that the temperature and time is sufficient to obtain a sterile product, meaning for example at least 20 minutes at a temperature of at least 121 degrees C. Lock, membrane, cylinder, plug, tubings and coupling can be made of bio-compatible plastic material.

Column house completely or partially filled with the filtration material according to the invention and equipped with above mentioned closed tubing set and plug can be autoclaved, steam sterilized and or sterilized with alkaline solution. This facilitates according to the invention the achievement of sterility of the material according to the invention. With earlier methods sterile (aseptic) production and filling conditions have been attempted, which are difficult to achieve.

What is claimed is:

1. An autoclavable filtration material comprising:
   a saccharide coupled to a spacer; and
   a matrix coupled to the spacer, the matrix being a cross-linked agarose;
   wherein the spacer comprises the following formula:

$$-N(Acetyl)-(CH_2)_n NH-,$$

wherein n is an integer selected from 0, 1, 2, 3, 4, 5, 6, or 7.

2. An autoclavable filtration material comprising:
   a saccharide coupled to a spacer; and
   a matrix coupled to the spacer, the matrix being a cross-linked agarose;
   wherein the spacer comprises the following formula:

$$-O(CH_2)_n PhNH-,$$

Or $$-N(Acetyl)-(CH_2)_n NH-,$$

wherein n is an integer selected from 1, 2, 3, 4, 5, 6, or 7.

3. The filtration material of claim 1 or 2, further comprising a second spacer attached to the matrix.

4. The filtration material of claim 1 or 2, wherein the matrix is bound to two or more molecules of saccharide.

5. The filtration material of claim 1 or 2, wherein the bound saccharide ranges from 0.01 to 20 mole per liter of matrix.

6. The filtration material of claim 1 or 2 comprising at least one of a Blood group A determinant and a Blood group B determinant bound to matrix.

7. The filtration material of claim 1 or 2, wherein the saccharide binds a pathogen.

8. The filtration material of claim 1 or 2, wherein the saccharide binds an antibody, a cancer-antigen, a toxin, a bacteria, or a virus.

9. The filtration material of claim 1 or 2, wherein the filtration material is in the form of particles.

* * * * *